United States Patent
Wallace et al.

(12) 
(10) Patent No.: US 6,603,994 B2
(45) Date of Patent: Aug. 5, 2003

(54) APPARATUS AND METHOD FOR INTERNALLY INDUCING A MAGNETIC FIELD IN AN ANEURYSM TO EMBOLIZE ANEURYSM WITH MAGNETICALLY-CONTROLLABLE SUBSTANCE

(75) Inventors: Michael P. Wallace, Fremont, CA (US); Joseph C. Eder, Los Altos Hills, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 51 days.

(21) Appl. No.: 09/752,747

(22) Filed: Dec. 28, 2000

(65) Prior Publication Data

US 2002/0087077 A1 Jul. 4, 2002

(51) Int. Cl.⁷ .................................................. A61B 6/00
(52) U.S. Cl. .............................. 600/434; 600/9; 600/11; 600/13; 600/114; 600/117; 600/427; 600/433; 600/431; 600/12; 361/143; 361/146; 604/891.1
(58) Field of Search .................. 600/12, 433, 434, 600/431, 9, 11, 13, 114, 117, 407, 420, 424, 427, 429, 410, 374; 361/141, 143, 146; 348/77; 604/891.1

(56) References Cited

U.S. PATENT DOCUMENTS

| 5,122,136 | A | | 6/1992 | Guglielmi et al. |
| 5,250,071 | A | | 10/1993 | Palermo |
| 5,895,385 | A | * | 4/1999 | Guglielmi et al. ............ 606/32 |
| 5,984,929 | A | | 11/1999 | Bashiri et al. |
| 6,014,580 | A | | 1/2000 | Blume et al. |
| 6,032,677 | A | * | 3/2000 | Blechman et al. .......... 128/899 |
| 6,123,714 | A | | 9/2000 | Gia et al. |
| 6,190,373 | B1 | * | 2/2001 | Palermo et al. ................. 606/1 |
| 6,364,823 | B1 | * | 4/2002 | Garibaldi et al. ............. 600/12 |
| 6,375,606 | B1 | * | 4/2002 | Garibaldi et al. ............. 600/12 |

FOREIGN PATENT DOCUMENTS

| WO | WO 00/07641 | 2/2000 |
| WO | WO 00/54832 | 9/2000 |
| WO | WO 00/54835 | 9/2000 |
| WO | WO 01/15608 A1 | 3/2001 |

* cited by examiner

*Primary Examiner*—Marvin M. Lateef
*Assistant Examiner*—Devaang Shah
(74) *Attorney, Agent, or Firm*—Bingham McCutchen LLP

(57) ABSTRACT

The present invention involves a magnetic embolization apparatus for embolizing an aneurysm of a blood vessel. The apparatus includes a coiled element adapted for insertion within an aneurysm of a blood vessel, the coiled element shaped to be retained within the aneurysm, and one or more permanent magnetic segments carried by the coiled element to internally induce a magnetic field from within the aneurysm to control a magnetic field controllable embolic to embolize the aneurysm.

50 Claims, 4 Drawing Sheets

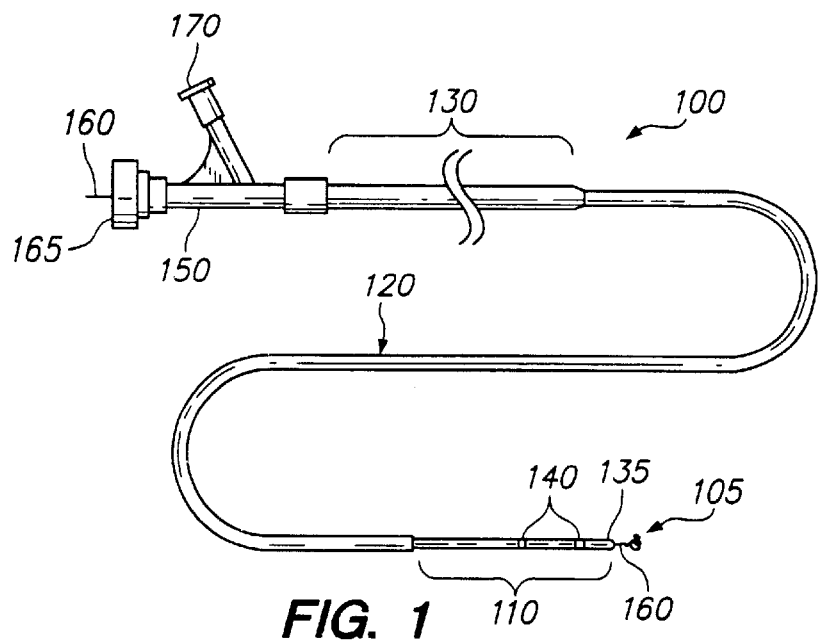
FIG. 1
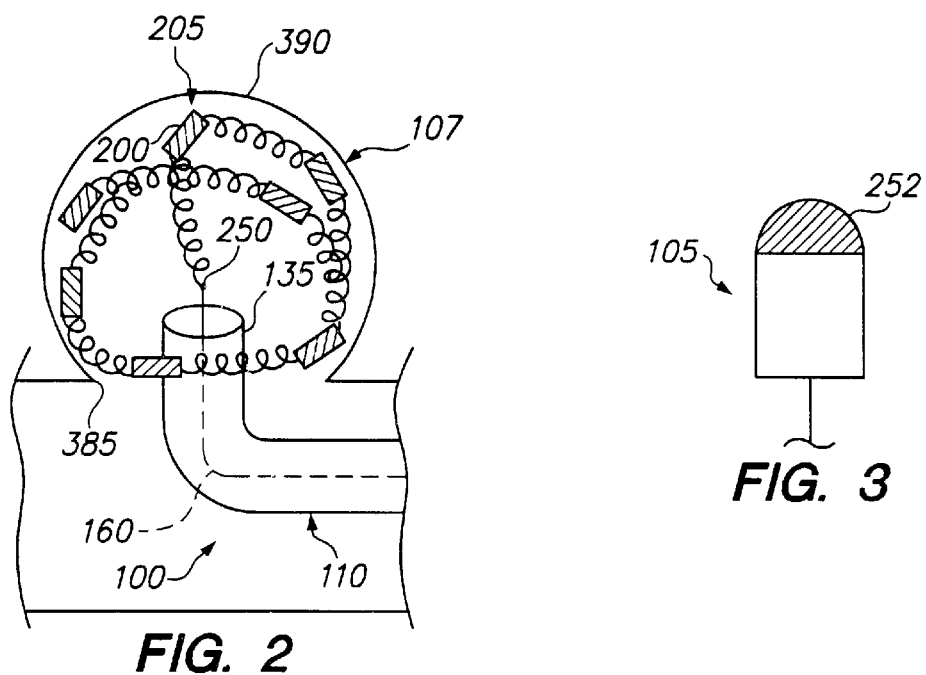
FIG. 2
FIG. 3
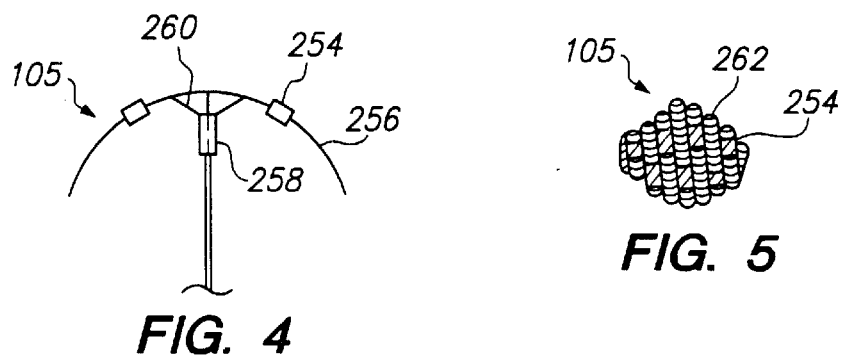
FIG. 4
FIG. 5

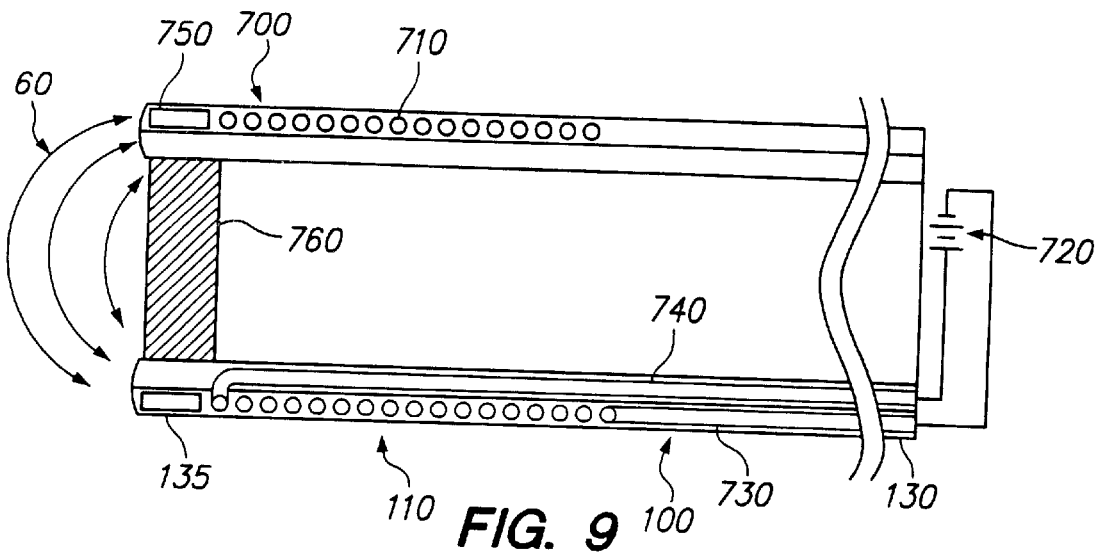
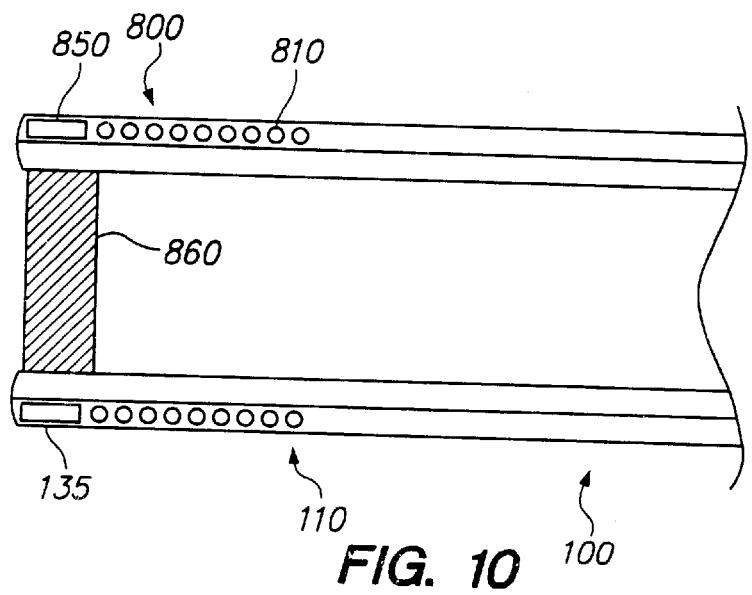

APPARATUS AND METHOD FOR INTERNALLY INDUCING A MAGNETIC FIELD IN AN ANEURYSM TO EMBOLIZE ANEURYSM WITH MAGNETICALLY-CONTROLLABLE SUBSTANCE

FIELD OF THE INVENTION

The invention relates, in general, to an apparatus and method for forming an occlusion in a mammalian body, and, in particular to an apparatus and method for internally inducing a magnetic field in an aneurysm to embolize the aneurysm with a magnetically-controllable substance.

BACKGROUND

Like all parts of the body, the brain is composed of living cells that require a blood supply to provide oxygen and nutrients. A hemorrhage in a blood vessel in the brain or in the space closely surrounding the brain is a common cause of strokes. Hemorrhage refers to bleeding into the brain, usually because of a problem with a blood vessel. The problem is often an aneurysm.

An aneurysm is an abnormal bulging outward of blood vessel wall. The wall may smoothly bulge outward in all directions (a fusiform aneurysm) or it may form a sack arising from one wall (a saccular aneurysm). If the aneurysm ruptures, a hemorrhage occurs. This can compress and irritate the surrounding blood vessels, resulting in a reduced supply of oxygen and nutrients to the cells, possibly causing a stroke.

Aneurysms can be treated from outside the blood vessel using surgical techniques or from inside the blood vessel using endovascular techniques. Endovascular treatment of an aneurysm is performed using a catheter. X-ray, magnetic resonance imaging (MRI) equipment, or other visualization equipment may be used to view the progress during the procedure.

A magnetically directable embolic such as an acrylic, iron-containing glue as to fill or obliterate aneurysms. The embolic is delivered by means of a catheter and is directed into an aneurysm with an external magnetic field generated by a permanent magnet or electromagnetic device used for Stereotaxis procedures such as a prototype device made by Stereotaxis Inc. of St. Louis, Mo. An example of such a device is shown and described in U.S. Pat. No. 6,014,580 to Blume, et al. Problems with this approach include that the Stereotaxis machine is cumbersome and expensive and, in some cases, the external magnetic field produced by the Stereotaxis machine is not strong enough to control delivery of the iron-containing, magnetically-directable glue into the aneurysm.

SUMMARY OF THE INVENTION

An aspect of the present invention involves a magnetic embolization apparatus for embolizing an aneurysm of a blood vessel. The apparatus includes a coiled element adapted for insertion within an aneurysm of a blood vessel, the coiled element shaped to be retained within the aneurysm, and one or more permanent magnetic segments carried by the coiled element to internally induce a magnetic field from within the aneurysm to control a magnetic field controllable embolic to embolize the aneurysm.

An additional aspect of the present invention involves a magnetic embolization apparatus for embolizing an aneurysm of a blood vessel. The apparatus includes a coiled element adapted for insertion within an aneurysm of a blood vessel, the coiled element shaped to be retained within the aneurysm, and one or more permanent magnetic segments carried by the coiled element to internally induce a magnetic field from within the aneurysm to control a magnetic field controllable embolic to embolize the aneurysm.

A further aspect of the present invention involves a magnetic embolization apparatus for embolizing an aneurysm of a blood vessel. The apparatus includes an element adapted for insertion within an aneurysm of a blood vessel, the element shaped to be retained within a dome of the aneurysm, and one or more permanent magnetic segments carried by the element in a location so as to be located in a top, central part of the dome of the aneurysm and adapted to internally induce a magnetic field from within the aneurysm to control a magnetic field controllable embolic to embolize the aneurysm.

Another aspect of the invention involves a magnetic embolization apparatus for embolizing an aneurysm of a blood vessel. The apparatus includes an element adapted for insertion within an aneurysm of a blood vessel, an electromagnet carried by the element to internally induce a magnetic field from within the aneurysm to control a magnetic field controllable embolic to embolize the aneurysm, and a guide wire having a lead wire for supplying electrical current to the electromagnet and a return wire for returning electrical current from the electromagnet.

An additional aspect of the invention involves a magnetic embolization apparatus for embolizing an aneurysm of a blood vessel. The apparatus includes a catheter including a distal portion adapted for insertion within an aneurysm of a blood vessel, and an electromagnet carried by the distal portion of the catheter to internally induce a magnetic field from within the aneurysm to control a magnetic field controllable embolic to embolize the aneurysm.

A further aspect of the invention involves a magnetic embolization apparatus for embolizing an aneurysm of a blood vessel. The apparatus includes a catheter having a distal portion adapted for insertion within an aneurysm of a blood vessel, and a permanent magnet carried by the distal portion of the catheter to internally induce a magnetic field from within the aneurysm to control a magnetic field controllable embolic to embolize the aneurysm.

Another aspect of the invention involves a magnetic embolization apparatus for embolizing an aneurysm of a blood vessel. The apparatus includes a guide wire including a distal end, a catheter including a distal portion adapted for insertion within an aneurysm of a blood vessel and an elongated lumen slidably receiving the guide wire and adapted to deliver a magnetic field controllable embolic to the aneurysm, an element connected to the distal end of the guide wire, the element adapted for insertion within the aneurysm, and a magnet carried by the element to internally induce a magnetic field from within the aneurysm to control the magnetic field controllable embolic to embolize the aneurysm.

A further aspect of the present invention involves a magnetic embolization apparatus for embolizing an aneurysm of a blood vessel. The apparatus includes a guide wire having a distal end, a catheter including a distal portion adapted for insertion within an aneurysm of a blood vessel and including first and second lumens, the first lumen slidably receiving the guide wire and the second lumen adapted to deliver the magnetic field controllable embolic to the aneurysm, an element connected to the distal end of the guide wire, the element adapted for insertion within the aneurysm, and a magnet carried by the element to internally induce a magnetic field from within the aneurysm to control the magnetic field controllable embolic to embolize the aneurysm.

An additional aspect of the present invention involves a method of embolizing an aneurysm of a blood vessel. The method includes delivering a magnetic embolization apparatus into an aneurysm with a lumen of a catheter, delivering a magnetic-field controllable embolic within the aneurysm with the same lumen of the catheter, and internally inducing a magnetic field with the magnetic embolization apparatus from within the aneurysm to control the magnetic-field controllable embolic to embolize the aneurysm.

Another aspect of the present invention involves a method of embolizing an aneurysm of a blood vessel. The method includes delivering a magnetic embolization apparatus into an aneurysm with a first lumen of a catheter, delivering a magnetic-field controllable embolic within the aneurysm with a second, different lumen of the same catheter, and internally inducing a magnetic field with the magnetic embolization apparatus from within the aneurysm to control the magnetic-field controllable embolic to embolize the aneurysm.

A still further aspect of the present invention involves a method of embolizing an aneurysm of a blood vessel. The method includes delivering a magnetic embolization apparatus into an aneurysm with a first catheter, delivering a magnetic-field controllable embolic within the aneurysm with a second, different catheter, and internally inducing a magnetic field with the magnetic embolization apparatus from within the aneurysm to control the magnetic-field controllable embolic to embolize the aneurysm.

Other features and advantages of the invention will be evident from reading the following detailed description, which is intended to illustrate, but not limit, the invention.

BRIEF DESCRIPTION OF THE DRAWINGS

The drawings illustrate the design and utility of preferred embodiments of the present invention, in which similar elements are referred to by common reference numerals.

FIG. 1 is a side-elevational view of an embodiment of a catheter that may be used with the magnetic embolization apparatus.

FIG. 2 is a side-elevational view of a distal portion of the catheter illustrated in FIG. 1 in a blood vessel with an embodiment of the magnetic embolization apparatus shown disposed in an aneurysm.

FIGS. 3–5 illustrate alternative embodiments of the magnetic embolization apparatus.

FIG. 9 is a cross-sectional view of a distal portion of a catheter including a further embodiment of a magnetic embolization apparatus disposed therein.

FIG. 10 is a cross-sectional view of a distal portion of a catheter including a still further embodiment of a magnetic embolization apparatus disposed therein.

DETAILED DESCRIPTION OF THE PREFERRED EMBODIMENTS

Figure 6:
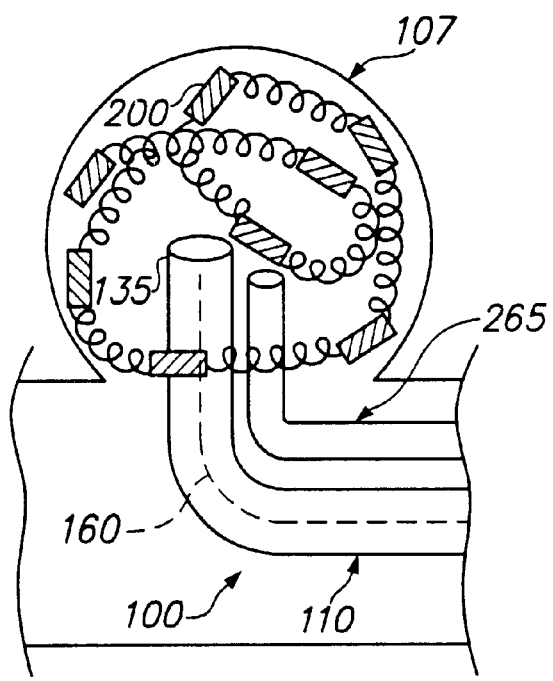
FIG. 6 is a view similar to FIG. 2, but with a magnetically directable embolic delivery catheter shown next to the magnetic embolization apparatus catheter.

With reference to FIG. 1, an exemplary multi-section catheter 100 that may be used to deliver and deploy a magnetic embolization apparatus 105, which is constructed in accordance with an embodiment of the invention, at a targeted aneurysm 107 (FIG. 2) will now be described. Although the invention will be described in terms of aneurysm treatment, it may also be adaptable for endovascular occlusion in arteries, veins, vascular malformations, and arteriovenous fistulas. The invention may also be used for forming an occlusion in other areas of a mammalian body.

The catheter 100 includes a distal section 110, an intermediate section 120, and a proximal section 130. The sections decrease in flexibility from the proximal section 130 to the distal section 110.

The distal section 110 is very flexible and soft to allow deep penetration into the extraordinary convolutions of the neurological vasculature without trauma. The magnetic embolization apparatus 105 is deployed from the distal section 110 of the catheter 100 at a distal end 135. The distal section 110 may include one or more radio-opaque bands 140 to allow viewing of the position of the distal section under fluoroscopy.

A luer assembly 150 at the proximal section 130 of the catheter 100 accomodates a pusher, core, or guide wire 160. The wire 160 may be made of any well-known guide wire material in the art such as stainless steel. The magnetic embolization apparatus 105 may be attached to a distal end of the wire 160. The luer assembly 150 may also include a fluid port 165 for introducing and/or removing a magnetically controllable embolization substance and a power port 170 for connecting the catheter 100 to a power supply. The catheter 100 may also include any well-known steering assembly in the art for delivering the magnetic embolization apparatus 105 to the targeted aneurysm 107.

With reference to FIG. 2, an embodiment of the magnetic embolization apparatus 105 will now be described. The apparatus 105 includes one or more magnetic segments 200 attached to an element shaped to retain or secure the apparatus 105 within the aneurysm 107. The permanent magnetic segments 200 (and the permanent magnets described below) may be made out of a material that safely dissolves over time or loses its magnetization over time so that MRJ may be used post surgery. In the embodiment shown, the element is a Guglielmi Detachable Coil (GDC®) assembly 205 made of platinum and sold by Target Therapeutics, Inc. of Fremont, Calif. When the coil assembly 205 is deployed into the aneurysm 107, the coil assembly 205 preferably has a convoluted configuration. This three-dimensional, convoluted configuration helps to secure the apparatus 105 in the aneurysm 107.

In a preferred embodiment, the coil assembly 205 is detachably coupled to the wire 160 by a detachment mechanism 250. Examples of detachment mechanisms that may be used include a mechanical detachment mechanism such as that described in U.S. Pat. No. 5,250,071 ("the '71 patent") to Palermo and an electrolytic detachment mechanism such as those described in U.S. Pat. No. 5,122,136 ("the '136 patent") to Guglielmi, et al. and U.S. Pat. No. 6,123,714 ("the '714 patent) to Gia, et al. The '71, '136, and '714 patents are incorporated by reference as though set forth in full. Preferably, an electrolytic detachment mechanism similar to those described in the '136 patent or the '714 patent is used. An electrolytic detachment mechanism includes an electrolytic, sacrificial joint that separates when a small electric current is applied therethrough. The '136 patent describes a soldered electrolytic, sacrificial joint and the '714 patent describes a solderless electrolytic, sacrificial joint. The wire 160 is preferably fine enough to allow an embolic to be delivered through the same lumen that the wire 160 is disposed within.

Although the magnetic embolization apparatus 105 has been described as having a three-dimensional, convoluted configuration, in alternative embodiments, the apparatus 105 may include other configurations. For example, with reference to FIG. 3, the magnetic embolization apparatus 105 may have a generally bullet-shaped configuration with a partially spherical magnetic section 252. Alternatively, the apparatus 105 illustrated in FIG. 3 may have a completely spherical configuration and magnetic section. With reference to FIG. 4, the apparatus 105 may have an umbrella-like configuration with magnetic segments 254 located on struts 256 of the apparatus 105. To deploy or retract the struts 256, a reciprocating base 258 may be coupled to a control device (not shown) for controlling arms 260 of the apparatus 105. Alternatively, struts may carry a magnetic, generally hemispherical dome member. With reference to FIG. 5, the apparatus 105 may include a diamond-shape fibered platinum coil assembly 262 sold by Target Therapeutics, Inc. of Fremont, Calif. All of the embodiments of the apparatus 105 described above have advantageous configurations because, once deployed in the aneurysm 107, they concentrate the magnetic field near a central part of the dome 390 of the aneurysm 107. This helps to draw the magnetically controllable embolic deeper into the aneurysm 107, away from a neck 385 of the aneurysm 107. This reduces the chances of the embolic escaping the aneurysm 107 or the embolic or portions of the embolic dislodging from the aneurysm 107. It should also be noted that the apparatus 105 may come in a variety of sizes to accommodate different size aneurysms 107 and/or a variety of configurations to accommodate aneurysms 107 having different shapes.

With reference back to FIG. 2, the magnetic embolization apparatus 105 will now be described in use. The catheter 100 is introduced into the vasculature of a patient via a cannula or introducer sheath and snaked through the vasculature of the patient to the targeted aneurysm 107 by any well-known method in the art. X-ray, fluoroscopy or other well-know visualization techniques may be used to assist the physician in directing the catheter 100 to the targeted aneurysm 107. The catheter 100 may be introduced over a guide wire such as the guide wire 106 to facilitate delivery of the catheter 100 to the targeted aneurysm 107. During delivery of the distal portion 110 of the catheter 100 to the aneurysm site, the apparatus 105 may be located in the catheter 100, for example, in the distal portion 110 of the catheter 100. Alternatively, the apparatus 105 may be introduced through the catheter 100 with the help of the wire 160 after the catheter 100 is directed to the targeted aneurysm site. The distal end 135 of the catheter 100 may be positioned at the aneurysm site adjacent the neck 385 of the aneurysm 107, at the neck 385 of the aneurysm 107, or within the aneurysm 107.

Once the distal end 135 of the catheter 100 is delivered to the aneurysm 107, the apparatus 105 may be deployed within the aneurysm 107. This may be accomplished by advancing the pusher wire 160 distally through the catheter 100. Preferably, the apparatus 105 has a pre-shaped memory so that the apparatus 105 will automatically deploy into the convoluted, three-dimensional configuration shown in FIG. 2 when the apparatus 105 is advanced into the aneurysm 107. In an alternative embodiment, the catheter 100 may include a sheath that is retracted to deploy the apparatus 105. In the embodiments of the apparatus 105 illustrated in FIGS. 3–5, the apparatus 105 is positioned in the aneurysm 107 so that the magnet portion 252, 254, 260 is positioned near a top center of the dome 390 of the aneurysm 107. The configuration of the apparatus 105 helps to secure the apparatus 105 within the aneurysm 107.

Next, the distal end 135 of the catheter 100 is centered within the dome 390 of the aneurysm 107, and a magnetically controllable embolic such as an acrylic, iron-containing glue that hardens over time is delivered to the aneurysm 107 via the same lumen of the catheter 100 as that through which the apparatus 105 and the wire 160 are introduced. In an alternative embodiment, the embolic may have a different composition. For example, the embolic may be made of a composition that loses its magnetic controllability so that MRI may be used post surgery. The one or more permanent magnets 200 of the apparatus 105 internally attracts, from within the aneurysm 107, the iron-containing embolic to the one or more magnets 200 at the dome 390 of the aneurysm 107, filling the aneurysm 107. The apparatus 105 may be detached from the wire 160 using the detachment mechanism 250 before or after the embolic is delivered to the aneurysm 107. Further, if the apparatus 105 is detached from the wire 160 after the embolic is delivered to the aneurysm 107, the apparatus 105 may be detached from the wire 160 after the embolic has sufficiently hardened or polymerized in the aneurysm 107.

The apparatus 105 is left in the aneurysm 107 and the catheter 100 is withdrawn from the patient's body. In an alternative embodiment, the apparatus 105 may not be detached from the wire 160 (no detachment mechanism 250) after the apparatus 105 is deployed in the aneurysm 107. The magnetically controllable embolic may be introduced into the aneurysm 107 after the apparatus 105 is deployed in the aneurysm 107, and after a period of time that is sufficient to magnetically induce the embolic to fill the aneurysm 107 and allow the embolic to partially polymerize, the apparatus is retracted into the distal portion 110 of the catheter 100 and the catheter 100 is withdrawn with the apparatus 105 therein.

With reference to FIG. 6, in an alternative apparatus and embolic delivery method, the catheter 100 may be used to deliver and deploy the apparatus 106 to the targeted aneurysm site in the manner described above, and, instead of deliverying the magnetically controllable embolic through the same catheter, a separate embolic delivery catheter 265 may be used to deliver the embolic to the aneurysm 107.

Figure 7:
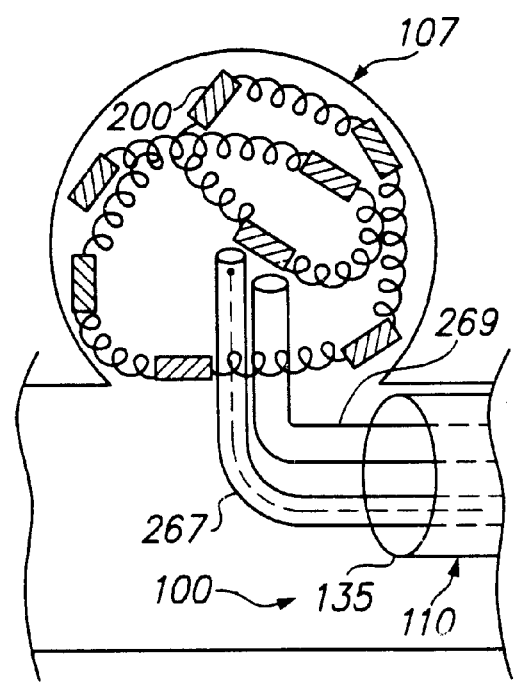
FIG. 7 is view similar to FIG. 2, but with an embodiment of a dual lumen catheter shown.

With reference to FIG. 7, in a further embodiment, the catheter 100 may be a dual-lumen catheter defined by respective lumen walls. The apparatus 105 may be delivered to the targeted aneurysm 107 using the wire 160 via a first lumen 267, and the magnetically controllable embolic may be delivered to aneurysm 107 via a second lumen 269.

Although the magnetic embolization apparatus 105 has been described as including a permanent magnet 200, in alternative embodiments, the detachable embolization apparatus may include an electromagnet that is used to internally induce a magnetic field within the aneurysm 107 for embolizing the aneurysm 107 by running electrical current through the electromagnet.

Figure 8:
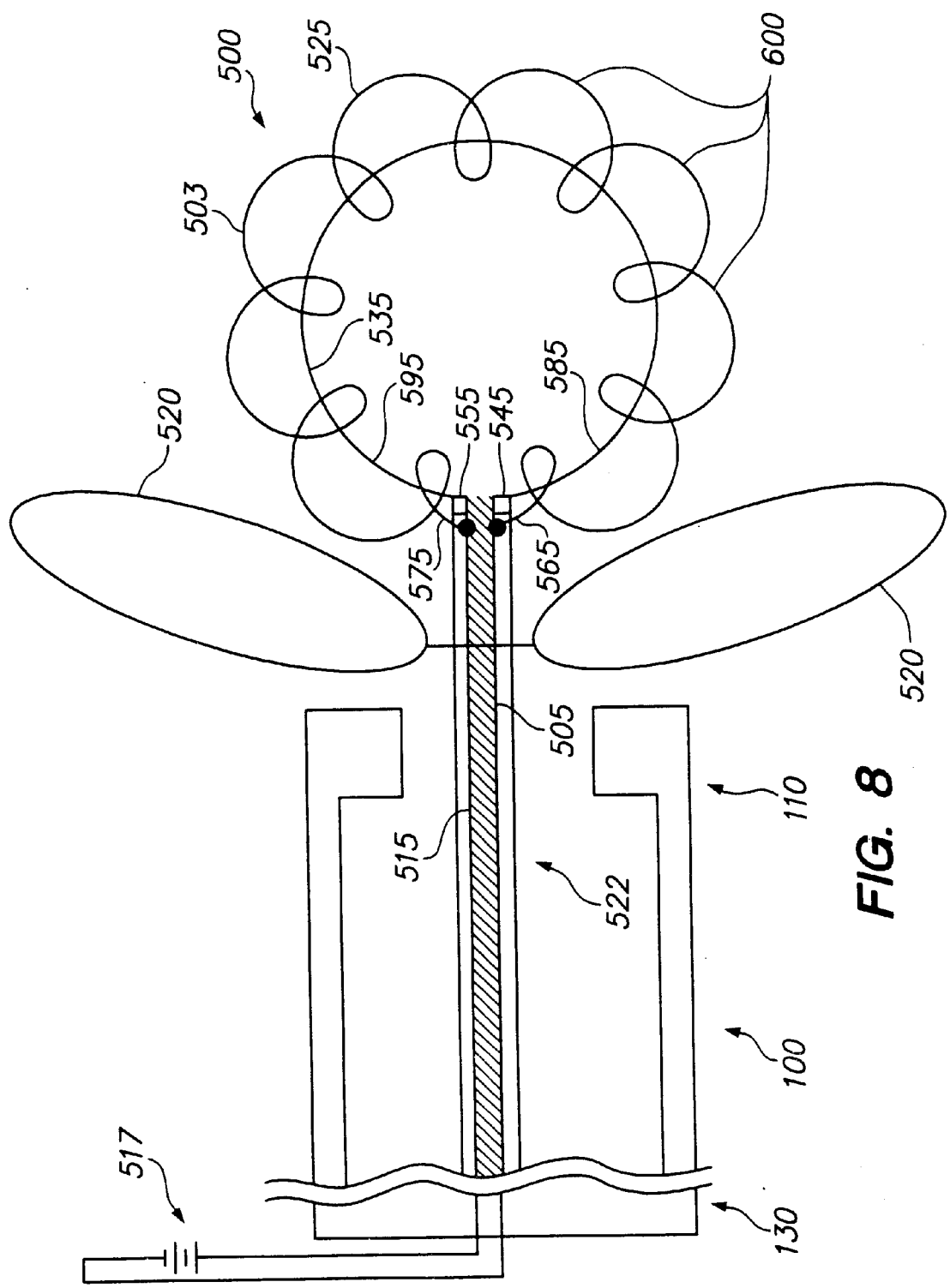
FIG. 8 is side-elevational view of a distal portion of a catheter with a further embodiment of a magnetic embolization apparatus shown.

For example, with reference to FIG. 8, an embodiment of an electromagnetic detachable embolization apparatus 500 is shown. The apparatus 500 includes a curvilinear, toroid-shaped electromagnet 503 and a pair of wire loops 520 to help secure the apparatus 500 within the aneurysm 107. In alternative embodiments, the electromagnet may have different configurations besides a toroidal, curvilinear configuration. The electromagnet 503 and the wire loops 520 are coupled to a guide wire 522. The guide wire 522 may include an insulated lead wire 505 and return wire 515 coupled to a power source 517 near the proximal section 130 of the catheter 100. Although not shown, the guide wire 522 may include a detachment mechanism, as described above.

The electromagnet 503 includes a main wire 525, an insulated structural support wire 535, a first insulating separator 545, and a second insulating separator 555. The main wire 525 has a lead end 565 electrically connected to the lead wire 505 and a return end 575 electrically connected to the return wire 515. The first insulating separator 545 connects the lead wire 505 to a first portion 585 of the insulated structural support wire 535 and the second insulating separator 555 connects the return wire 515 to a second portion 595 of the insulated structural support wire 535. The main wire 525 includes numerous coils 600 that together form the curvilinear, toroid shape of the electromagnet 503.

In use, the catheter 100 is snaked through the vasculature of the patient to a targeted aneurysm 107 with the electromagnetic embolization apparatus 500 collapsed within the distal portion 100 of the catheter 100. The apparatus 500 is deployed within the aneurysm 107 so that the electromagnet 503 is positioned near a top center of the dome 390 of the aneurysm 107. The wire loops 520 hold the apparatus 500 securely within the aneurysm 107. Current supplied by the power source 517 through the insulated lead wire 505 flows through the electromagnet 503, electromagnetically and internally inducing a magnetic field in the aneurysm 107. The current returns throughout the return wire 515. In an alternative embodiment, the current may be returned through a return wire in the catheter body; however, returning the current through the wire 160 is more efficient.

Next, the magnetically controllable embolic is delivered to the aneurysm 107. This may be done via the same catheter 100 as illustrated in FIG. 2, a separate embolic deliver catheter 265 as illustrated in FIG. 6, or a dual lumen catheter 100 as illustrated in FIG. 7. The electromagnet 503 of the apparatus 500 attracts the iron-containing embolic to the electromagnet 503, filling the aneurysm 107. Once the aneurysm 107 is filled a sufficient amount and the embolic has hardened or polymerized a sufficient amount, the apparatus 500 may be detached, if a detachment mechanism exists, and left impregnated in the hardened embolic, within the aneurysm 107.

In an alternative embodiment, the apparatus 500 may not be detached from the guide wire 522 (no detachment mechanism) after the apparatus 500 is deployed in the aneurysm 107. The magnetically controllable embolic may be introduced into the aneurysm 107 after the apparatus 500 is deployed in the aneurysm 107, and after a period of time that is sufficient to magnetically induce the embolic to fill the aneurysm 107 and allow the embolic to polymerize, the apparatus 500 is retracted into the distal portion 110 of the catheter 100 and the catheter 100 is withdrawn with the apparatus 500 therein.

With reference to FIG. 9, an embodiment of a magnetic embolization apparatus 700 constructed in accordance with a further embodiment of the invention will now be described. The apparatus 700 includes a coiled electromagnet 710 located in the catheter body in the distal portion 110 of the catheter 100. Electrical current is supplied to the electromagnet 710 by a power source 720 via a lead wire 730 and is returned by a return wire 740. A radio-opaque marker 750 may be located in the catheter body at the distal end 135 of the catheter 100 to assist in locating the distal portion 110 of the catheter 100 in the vasculature of the patient using fluoroscopy. A plug 760 may be located in the distal end 135 of the catheter 100 to prevent the magnetically directable embolic from being magnetically drawn into the distal portion 110 of the catheter 100 when the electromagnet 710 is actuated.

In use, the catheter 100 is snaked through the vasculature of the patient to the targeted aneurysm 107. At the aneurysm 107, the distal end 135 of the catheter 100 is positioned into the aneurysm 107, near the dome 390. The radio-opaque marker 135 may be used with conventional fluoroscopy equipment to assist in positioning the distal end 135 of the catheter 100. The distal end of a separate embolic deliver catheter 265, as illustrated in FIG. 6, may be positioned in the aneurysm 107, adjacent the catheter 100, for delivering a magnetically controllable embolic to the aneurysm 107. Alternatively, as illustrated in FIG. 7, the catheter 107 may be a dual lumen catheter with one lumen/lumen wall having a configuration similar to the catheter 100 illustrated in FIG. 9 and an adjacent lumen/lumen wall configured to deliver the embolic to the aneurysm 107. Current is supplied by the power source 720 through the lead wire 730 to actuate the electromagnet 710, electromagnetically and internally inducing a magnetic field 760 in the aneurysm 107. The current returns throught the return wire 740. The magnetically controllable embolic is delivered to the aneurysm 107. The electromagnet 710 of the apparatus 500 attracts the iron-containing embolic along the magnetic field lines 760 induced by the electromagnet 503, filling the aneurysm 107. Once the aneurysm 107 is filled a sufficient amount and the embolic has hardened or polymerized a sufficient amount, the magnetic field 760 may be terminated by cutting off power to the electromagnet 710, and the catheter 100 may be withdrawn. Advantages of this embodiment include a guide wire is not required to deliver the magnetic embolization apparatus, the apparatus 700 is not left in the aneurysm 107 after embolization, and the apparatus 700 does not have to be withdrawn through a partially or fully polymerized embolic in the aneurysm 107.

With reference to FIG. 10, an embodiment of a magnetic embolization apparatus 800 constructed in accordance with a still further embodiment of the invention will now be described. The apparatus 800 includes a coiled permanent magnet 810 located in the catheter body in the distal portion 110 of the catheter 100. Although magnetic configurations other than a coiled magnet may be used, a coiled magnet configuration or similar configuration is advantageous for providing the distal portion 110 of the catheter 100 with the requisite flexibility and to minimize catheter tip stiffness. A radio-opaque marker 850 may be located in the catheter body at the distal end 135 of the catheter 100 to assist in locating the distal portion 110 of the catheter 100 in the vasculature of the patient using fluoroscopy. A plug 860 may be located in the distal end 135 of the catheter 100 to prevent the magnetically directable embolic from being magnetically drawn into the distal portion 110 of the catheter 100.

The method of use for the permanent magnetic embolization apparatus 800 is the same as that for the electromagnetic embolization apparatus 700, except that current is not supplied to the permanent magnet 810 to induce a magnetic field because a magnetic field always exists at the distal portion 100.

In a further embodiment of the invention, the electromagnet 710 of FIG. 9 may be combined with the permanent magnet 810 of FIG. 10 in the distal portion 110 of the catheter 100 to induce a stronger magnetic field in the aneurysm 107.

The above-described embodiments of the invention internally induce a magnetic field, from within the aneurysm, to embolize the aneurysm with a magnetically-directable embolic. This eliminates the needs for a cumbersome and expensive superconducting electromagnetic device or large permanent magnet such as those used for Stereotaxis procedures and produces a stronger and more efficient magnetic field at the point of interest than that produced by such devices.

While embodiments and applications of this invention have been shown and described, it would be apparent to those in the field that many more modifications are possible without departing from the inventive concepts herein. The invention, therefore, is not to be restricted except in the spirit of the appended claims.

What is claimed is:

1. A magnetic embolization apparatus for embolizing an aneurysm of a blood vessel, comprising: a coiled element adapted for insertion within an aneurysm of a blood vessel, the coiled element shaped to be retained within the aneurysm; and one or more permanent magnetic segments carried by the coiled element to internally induce a magnetic field from within the aneurysm that controls a magnetic field controllable embolic to embolize the aneurysm.

2. The apparatus of claim 1, wherein the coiled element includes a convoluted, three-dimensional profile when deployed in the aneurysm.

3. The apparatus of claim 1, further including a detachment mechanism for detachably mounting the apparatus to a core wire.

4. The apparatus of claim 3, wherein the detachment mechanism is an electrolytic, sacrificial joint.

5. The apparatus of claim 1, wherein the apparatus is adapted to be removed from the aneurysm during or after embolization.

6. The apparatus of claim 1, wherein the element comes in a variety of sizes to accommodate different size aneurysms.

7. The apparatus of claim 1, wherein the element comes in a variety of configurations to accommodate different aneurysm configurations.

8. A magnetic embolization apparatus for embolizing an aneurysm of a blood vessel, comprising: an element adapted for insertion within an aneurysm of a blood vessel, the element shaped to be retained within a dome of the aneurysm; and one or more permanent magnetic segments carried by the element in a location so as to be located in a top, central part of the dome of the aneurysm, and adapted to internally induce a magnetic field from within the aneurysm that controls a magnetic field controllable embolic to embolize the aneurysm.

9. The apparatus of claim 8, wherein the element includes a generally bullet-like shape.

10. The apparatus of claim 8, wherein the element includes at least a partially spherical shape.

11. The apparatus of claim 8, wherein the element includes a generally umbrella-like shape.

12. The apparatus of claim 8, wherein the element includes a generally diamond-like shape.

13. The apparatus of claim 8, further including a detachment mechanism for detachably mounting a core wire to the apparatus.

14. The apparatus of claim 13, wherein the detachment mechanism is an electrolytic, sacrificial joint.

15. The apparatus of claim 8, wherein the apparatus is adapted to be removed from the aneurysm during or after embolization.

16. A magnetic embolization apparatus for embolizing an aneurysm of a blood vessel, comprising: an element adapted for insertion within an aneurysm of a blood vessel; an electromagnet carried by the element to internally induce a magnetic field from within the aneurysm that controls a magnetic field controllable embolic to embolize the aneurysm; and a guide wire having a lead wire for supplying electrical current to the electromagnet and a return wire for returning electrical current from the electromagnet.

17. The apparatus of claim 16, wherein the element is shaped to be retained within the aneurysm.

18. The apparatus of claim 16, further including a detachment mechanism for detachably mounting a core wire to the apparatus.

19. The apparatus of claim 18, wherein the detachment mechanism is an electrolytic, sacrificial joint.

20. The apparatus of claim 16, wherein the apparatus is adapted to be removed from the aneurysm after embolization.

21. A magnetic embolization apparatus for embolizing an aneurysm of a blood vessel, comprising: a catheter including a distal portion adapted for insertion within an aneurysm of a blood vessel; and an electromagnet carried by the distal portion of the catheter to internally induce a magnetic field from within the aneurysm that controls a magnetic field controllable embolic to embolize the aneurysm.

22. The apparatus of claim 21, wherein the distal portion includes a distal end and a plug disposed in the distal end to prevent a magnetically controllable embolic from being magnetically attracted into the distal portion of the catheter.

23. The apparatus of claim 21, wherein the distal portion of the catheter includes a radio-opaque element.

24. The apparatus of claim 21, wherein the distal portion of the catheter includes a permanent magnet.

25. The apparatus of claim 21, wherein the catheter is a dual lumen catheter including a first lumen and a second lumen, the first lumen carrying said electromagnet, and said second lumen adapted to deliver said embolic to said aneurysm.

26. A magnetic embolization apparatus for embolizing an aneurysm of a blood vessel, comprising: a catheter including a distal portion adapted for insertion within an aneurysm of a blood vessel; and a permanent magnet carried by the distal portion of the catheter to internally induce a magnetic field from within the aneurysm that controls a magnetic field controllable embolic to embolize the aneurysm.

27. The apparatus of claim 26, wherein the distal portion includes a distal end and a plug disposed in the distal end to prevent a magnetically controllable embolic from being magnetically attracted into the distal portion of the catheter.

28. The apparatus of claim 26, wherein the distal portion of the catheter includes a radio-opaque element.

29. The apparatus of claim 26, wherein the magnet is a coiled magnet.

30. The apparatus of claim 27, wherein the catheter is a dual lumen catheter including a first lumen and a second lumen, the first lumen carrying said magnet, and said second lumen adapted to deliver said embolic to said aneurysm.

31. A magnetic embolization apparatus for embolizing an aneurysm of a blood vessel, comprising: a guide wire including a distal end; a catheter including a distal portion adapted for insertion within an aneurysm of a blood vessel and an elongated lumen slidably receiving the guide wire and adapted to deliver a magnetic field controllable embolic to the aneurysm; an element connected to said distal end of said guide wire, the element adapted for insertion within the aneurysm; and a magnet carried by the element to internally induce a magnetic field from within the aneurysm that controls the magnetic field controllable embolic to embolize the aneurysm.

32. A magnetic embolization apparatus for embolizing an aneurysm of a blood vessel, comprising:
- a guide wire including a distal end;
- a catheter including a distal portion adapted for insertion within an aneurysm of a blood vessel and including first and second lumens, the first lumen slidably receiving the guide wire and the second lumen adapted to deliver the magnetic field controllable embolic to the aneurysm;
- an element connected to said distal end of said guide wire, the element adapted for insertion within the aneurysm; and
- a magnet carried by the element to internally induce a magnetic field from within the aneurysm to control the magnetic field controllable embolic to embolize the aneurysm.

33. A method of embolizing an aneurysm of a blood vessel, comprising: delivering a magnetic embolization apparatus into an aneurysm with a lumen of a catheter; delivering a magnetic-field controllable embolic within the aneurysm with the same lumen of the catheter, internally inducing a magnetic field with the magnetic embolization apparatus from within the aneurysm that controls the magnetic-field controllable embolic to embolize the aneurysm.

34. The method of claim 33, wherein the step of delivering includes deploying the apparatus within the aneurysm with the assistance of a guide wire and before the embolic has completely polymerized, removing the apparatus from the aneurysm using the guide wire.

35. The method of claim 33, wherein the magnetic embolization apparatus includes a distal portion of a catheter that includes a catheter wall that carries a magnet.

36. The method of claim 33, wherein the magnetic embolization apparatus is a permanent magnetic embolization apparatus.

37. The method of claim 33, wherein the magnetic embolization apparatus is an electromagnetic embolization apparatus.

38. The method of claim 33, wherein the magnetic embolization apparatus is a combination permanent and electromagnetic embolization apparatus.

39. A method of embolizing an aneurysm of a blood vessel, comprising:
- delivering a magnetic embolization apparatus into an aneurysm with a first lumen of a catheter;
- delivering a magnetic-field controllable embolic within the aneurysm with a second, different lumen of the same catheter;
- internally inducing a magnetic field with the magnetic embolization apparatus from within the aneurysm to control the magnetic-field controllable embolic to embolize the aneurysm.

40. The method of claim 39, wherein the step of delivering includes deploying the apparatus within the aneurysm with the assistance of a guide wire and before the embolic has completely polymerized, removing the apparatus from the aneurysm using the guide wire.

41. The method of claim 39, wherein the magnetic embolization apparatus includes a distal portion of a catheter that includes a catheter wall that carries a magnet.

42. The method of claim 39, wherein the magnetic embolization apparatus is a permanent magnetic embolization apparatus.

43. The method of claim 39, wherein the magnetic embolization apparatus is an electromagnetic embolization apparatus.

44. The method of claim 39, wherein the magnetic embolization apparatus is a combination permanent and electromagnetic embolization apparatus.

45. A method of embolizing an aneurysm of a blood vessel, comprising:
- delivering a magnetic embolization apparatus into an aneurysm with a first catheter;
- delivering a magnetic-field controllable embolic within the aneurysm with a second, different catheter;
- internally inducing a magnetic field with the magnetic embolization apparatus from within the aneurysm to control the magnetic-field controllable embolic to embolize the aneurysm.

46. The method of claim 45, wherein the step of delivering includes deploying the apparatus within the aneurysm with the assistance of a guide wire and before the embolic has completely polymerized, removing the apparatus from the aneurysm using the guide wire.

47. The method of claim 45, wherein the magnetic embolization apparatus includes a distal portion of a catheter that includes a catheter wall that carries a magnet.

48. The method of claim 45, wherein the magnetic embolization apparatus is a permanent magnetic embolization apparatus.

49. The method of claim 45, wherein the magnetic embolization apparatus is an electromagnetic embolization apparatus.

50. The method of claim 45, wherein the magnetic embolization apparatus is a combination permanent and electromagnetic embolization apparatus.

* * * * *